(12) United States Patent
Gooding et al.

(10) Patent No.: US 8,110,079 B2
(45) Date of Patent: Feb. 7, 2012

(54) ELECTROCHEMICAL SENSOR (75) Inventors: John Justin Gooding, Sydney (AU); Guozhen Liu, Sydney (AU)

(73) Assignee: NewSouth Innovations Pty Limited, Sydney NSW (AU)

( * ) Notice: Subject to any disclaimer, the term of this patent is extended or adjusted under 35 U.S.C. 154(b) by 538 days.

(21) Appl. No.: 12/293,272

(22) PCT Filed: Mar. 16, 2007

(86) PCT No.: PCT/AU2007/000337
§ 371 (c)(1),
(2), (4) Date: Mar. 23, 2009

(87) PCT Pub. No.: WO2007/106936
PCT Pub. Date: Sep. 27, 2007

(65) Prior Publication Data
US 2009/0218239 A1 Sep. 3, 2009

(30) Foreign Application Priority Data

Mar. 17, 2006 (AU) ................................ 2006901394

(51) Int. Cl.
*G01N 27/26* (2006.01)
(52) U.S. Cl. .................. 204/403.01; 204/403.02; 435/4; 435/7.1; 435/287.1; 435/287.2; 435/817; 436/501; 205/777.5; 205/792

(58) Field of Classification Search ............. 204/403.01, 204/403.02; 435/4, 7.1, 287.1, 287.2, 817; 436/501; 205/777.5, 792
See application file for complete search history.

(56) References Cited

U.S. PATENT DOCUMENTS

| 5,534,132 A | 7/1996 | Vreeke |
| 6,770,190 B1 | 8/2004 | Milanovski |
| 2006/0058254 A1* | 3/2006 | Dina et al. ...................... 514/44 |

FOREIGN PATENT DOCUMENTS

| EP | 0402126 A1 | 12/1990 |
| WO | 00/11474 A1 | 3/2000 |

OTHER PUBLICATIONS

Supplementary European Search Report mailed Apr. 7, 2009, issued in corresponding Application No. EP 07 71 8585.8, filed Mar. 16, 2007.
Kwon S.-J., et al., "An Electrochemical Immunosensor Using Ferrocenyl-Tethered Dendrimer," Analyst 131(3):402-406, Mar. 2006.

* cited by examiner

*Primary Examiner* — Bruce Bell
(74) *Attorney, Agent, or Firm* — Christensen O'Connor Johnson Kindness PLLC

(57) ABSTRACT

Disclosed herein is an electrochemical sensor for detecting an analyte. The sensor comprises an electrode, a redox active species that is electrochemically accessible to the electrode, and a binding moiety capable of associating with the analyte, wherein association of the binding moiety with the analyte affects the electrochemistry of the redox active species. Also disclosed herein is a method for detecting the presence of an analyte in a sample.

35 Claims, 6 Drawing Sheets

First Sensor

Second Sensor

First Sensor

Second Sensor

Sensor A

Sensor B

ELECTROCHEMICAL SENSOR

TECHNICAL FIELD

The present invention relates to electrochemical sensors for detecting the presence of an analyte in a sample.

BACKGROUND ART

A number of electrochemical techniques for detecting the presence of an analyte in a sample have been described. These techniques can be classified as catalytic, where a reaction of a modified electrode with the analyte produces a new species which can be detected electrochemically, or affinity based, where a binding reaction between the analyte and a binding partner is detected electrochemically.

When using affinity based techniques, an enduring challenge has been to detect that the binding event has occurred. Typically this is achieved using some sort of redox-labelled species that enables differentiation between before and after binding of the analyte. Typically, the redox-labelled species, labelled analyte and/or other reagents are added to the sample at some stage during the analysis in order for the binding event to be detected electrochemically. It is therefore necessary for the person using the sensor to intervene during the analysis. The need for user intervention necessitates that such sensors require skill to operate.

DISCLOSURE OF INVENTION

In a first aspect, the present invention provides an electrochemical sensor for detecting an analyte, the sensor comprising:
an electrode;
a redox active species that is electrochemically accessible to the electrode; and
a binding moiety capable of associating with the analyte;
wherein the association of the binding moiety with the analyte affects the electrochemistry of the redox active species.

In some embodiments, when the binding moiety associates with the analyte, the association of the binding moiety and analyte remains in situ, thereby affecting the electrochemistry of the redox active species.

In other embodiments, when the binding moiety associates with the analyte, the binding moiety is released from the sensor, and the release of the binding moiety affects the electrochemistry of the redox active species.

The electrochemical sensor of the present invention exploits the changes in electrochemistry of the redox active species which occur when the binding moiety associates with the analyte in order to detect the presence of the analyte in a sample. As the redox active species is electrochemically accessible to the electrode, it is provided as part of the sensor and the changes in its electrochemistry occur without the need to add additional redox active species (or species capable of reacting to generate a redox active species) during analysis of a sample. The changes in the electrochemistry of the redox active species can be detected electrochemically contemporaneously with the association of the binding moiety with the analyte.

Typically, the redox active species is bound to the electrode and the binding moiety is bound to the redox active species.

In a second aspect, the present invention provides an electrode, wherein a redox active species is bound to the surface of the electrode and is electrochemically accessible to the electrode, and a binding moiety capable of associating with an analyte is associated with the redox active species, and wherein association of the binding moiety with the analyte affects the electrochemistry of the redox active species.

The binding moiety may be associated with the redox active species in any manner such that association of the binding moiety with the analyte affects the electrochemistry of the redox active species. Typically, the binding moiety is bound to the redox active species.

In a first embodiment of the first aspect of the present invention (referred to below as the "first sensor"), the electrochemical sensor is for detecting an antibody, and the sensor comprises:
an electrode;
a redox active species that is electrochemically accessible to the electrode; and
a binding moiety capable of becoming bound to the antibody;
wherein binding of the antibody to the binding moiety affects the electrochemistry of the redox active species.

In the first sensor, the binding moiety is preferably at least part of an antigen (i.e. an antigen to which the antibody is capable of binding). Typically, the binding moiety comprises an epitope capable of becoming bound to the antibody. The binding moiety may consist of the epitope. Alternatively, the binding moiety may be the antigen itself.

In such embodiments, the binding moiety typically has a very high degree of selectivity for the antibody, and the sensor is therefore less susceptible to interference from other species which may be present in the sample tested.

In some embodiments, the epitope may be chemically synthesized. That is, the binding moiety may be a chemical analogue of an epitope of an antigen.

In a second embodiment of the first aspect of the present invention (referred to below as the "second sensor"), the electrochemical sensor is for detecting an antigen, and the sensor comprises:
an electrode;
a redox active species that is electrochemically accessible to the electrode; and
a binding moiety that is an antibody capable of binding to the antigen;
wherein detachment of the antibody from the sensor affects the electrochemistry of the redox active species.

Typically, the second sensor further comprises at least part of an antigen (i.e. an antigen to which the antibody is capable of binding), and the binding moiety is bound to the at least part of an antigen. Typically, the at least part of an antigen is bound to the redox active species and to the antibody binding moiety. The at least part of an antigen may comprise an epitope of the antigen. The at least part of an antigen is typically bound to the redox active species (either directly or, for example, by a short length alkyl chain).

Typically, in such embodiments, the redox active species is bound to the electrode, the at least part of an antigen is bound to the redox active species, and the binding moiety is bound to the at least part of an antigen. In such embodiments, when the electrode is placed in a sample containing the antigen, at least some of the antibody binding moiety binds to the antigen in the sample and is released from the at least part of an antigen (i.e. released from the sensor). Such sensors typically have a high degree of selectivity for the antigen, and have little susceptibility to interference from other species which may be present in the sample.

When the first sensor is exposed to a sample that contains the antibody, the antibody binds to the binding moiety. Without wishing to be bound by theory, the inventors believe that the electrochemistry of the redox active species is suppressed following binding, because ions in the sample are restricted from interacting with the redox active species as the relatively large antibody enfolds the redox active species and effectively "shields" the redox active species from ions in the sample. This suppression is detectable using electrochemical techniques and may be quantified. Thus, transduction of the affinity based recognition event (i.e. the antibody attaching to the binding moiety) is achieved simply by exposing the sensor to the sample and passing an electrical current through the electrode, and it is not necessary for a user to intervene.

When the second sensor is exposed to a sample that contains the antigen, a competition for the binding moiety (i.e. the antibody) occurs between the sensor and the antigen in the sample. As a result of this competition, at least some of the antibody binding moieties detach from the sensor, which results in the redox active species becoming more exposed to ions in the sample. Again, this is detectable using electrochemical techniques, and transduction of the affinity based recognition event may be achieved without user intervention.

The redox active species is typically bound to the electrode by a species that is a conduit for electron movement, for example, a molecular wire or a nanotube, both of which are rigid species that efficiently transfer electrons.

The electrochemical sensor of the present invention typically further comprises blocking agents, for example polyethylene glycol (PEG), bound to the surface of the electrode. These blocking agents prevent non-specific interactions from occurring at the electrode surface by masking the electrode surface. By preventing such interactions, the sensitivity and reliability of the electrochemical sensor of the present invention may be greatly increased.

The electrochemical sensor of the present invention typically further comprises a detector capable of detecting changes in the electrochemistry of the redox active species as a result of association of the binding moiety with the analyte. The change in the electrochemistry of the redox active species is typically detected by analysing changes in the ability of the electrode to oxidise and reduce the redox active species as the potential of the electrode is scanned anodically and cathodically respectively. The electrochemical sensor of the present invention typically further comprises an electrical power source and a display for displaying electrochemical readings from the electrode.

In a third aspect, the present invention provides a method for detecting the presence of an analyte in a sample, the method comprising the steps of exposing to the sample a binding moiety capable of becoming associated with the analyte, the binding moiety being associated with a redox active species that is electrochemically accessible to an electrode; and taking electrochemical measurements which indicate whether there is a change in the electrochemistry of the redox active species as a result of association of the binding moiety with the analyte.

In a first embodiment of the third aspect of the present invention, the method is for detecting the presence of an antibody in a sample, the method comprising the steps of exposing to the sample a binding moiety capable of becoming bound to the antibody, the binding moiety being associated with a redox active species that is electrochemically accessible to an electrode; and taking electrochemical measurements which indicate whether there is a change in the electrochemistry of the redox active species as a result of the antibody binding to the binding moiety.

In a second embodiment of the third aspect of the present invention, the method is for detecting the presence of an antigen in a sample, the method comprising the steps of exposing to the sample a binding moiety that is an antibody capable of binding to the antigen, the binding moiety being associated with a redox active species that is electrochemically accessible to an electrode; and taking electrochemical measurements which indicate whether there is a change in the electrochemistry of the redox active species as a result of the binding moiety disassociating from the redox active species.

The method of the first embodiment of the third aspect of the present invention may be carried out using the first sensor. Similarly, the method of the second embodiment of the third aspect of the present invention may be carried out using the second sensor.

In a fourth aspect, the present invention provides a method for detecting the presence of an analyte in a sample, the method comprising the steps of exposing to the sample the electrochemical sensor of the first aspect of the present invention; and taking electrochemical measurements which indicate whether there is a change in the electrochemistry of the redox active species as a result of association of the binding moiety with the analyte.

In the method of the third or fourth aspect of the present invention, the electrochemical measurements which indicate whether there is a change in the electrochemistry of the redox active species may be made during or after association of the binding moiety with any of the analyte present in the sample.

As mentioned above, it is not necessary for a user to perform further steps when testing a sample for the analyte. Accordingly, in some embodiments of the third and fourth aspects of the present invention, the method consists essentially of, or consists only of, the steps referred to above.

BRIEF DESCRIPTION OF THE DRAWINGS

In the following detailed description, the following Figures are referred to, in which.

MODES FOR CARRYING OUT THE INVENTION

The present invention will now be described in more detail by reference to embodiments for detecting an antibody or an antigen in a sample. As will be apparent to those skilled in the art, embodiments of the present invention described below can readily be modified to enable the invention to be utilised for detecting other analytes, such as pesticides, herbicides, toxic organic chemicals, drug compounds, pollutants, hormones, and signalling molecules, in a sample.

The electrochemical sensor of the first embodiment of the first aspect of the present invention (the "first sensor") is for detecting an antibody. The first sensor comprises an electrode, a redox active species that is electrochemically accessible to the electrode, and a binding moiety capable of becoming bound to the antibody. In such embodiments, when the sensor is exposed to a sample which contains the antibody, the antibody binds to the binding moiety and the electrochemistry of the redox active species is affected.

As used herein, a reference to exposing a sensor of the present invention to a sample, refers to exposing the sensor to the sample in a manner that would permit the binding moiety to associate with any of the analyte that may be present in the sample. Typically, in a sensor of the present invention, the redox active species is bound to the surface of the electrode and the binding moiety is bound to the redox active species, and the sensor is exposed to the sample by placing at least part of the electrode in the sample, thereby enabling the binding moiety to associate with any of the analyte present in the sample.

The electrochemical sensor of the second embodiment of the first aspect of the present invention (the "second sensor") is for detecting an antigen. The second sensor comprises an electrode, a redox active species that is electrochemically accessible to the electrode, and a binding moiety that is an antibody capable of binding to the antigen. In use, when the sensor is exposed to a sample which contains the antigen, at least some of the antibody binding moieties detach from the sensor, which affects the electrochemistry of the redox active species.

Typically, the second sensor further comprises at least part of an antigen to which the antibody binding moiety is capable of binding (an "antigen analogue"), and the binding moiety is bound to the antigen analogue on the sensor. In such embodiments, the second sensor may be essentially the same as embodiments of the first sensor in which the binding moiety is an antigen analogue, except that an antibody is bound to the antigen analogue. Unless otherwise specified, the specific embodiments of the second sensor described below will include an antigen analogue.

When using the second sensor, if the antigen is present in the sample, the sensor will show an increase in electrochemistry. Thus, a positive signal occurs when the electrode of the second sensor is exposed to a sample containing the antigen and an electrical current is passed through the electrode. In general, sensors which provide a positive signal are more desirable because they are less prone to giving false positive results.

Figure 1:
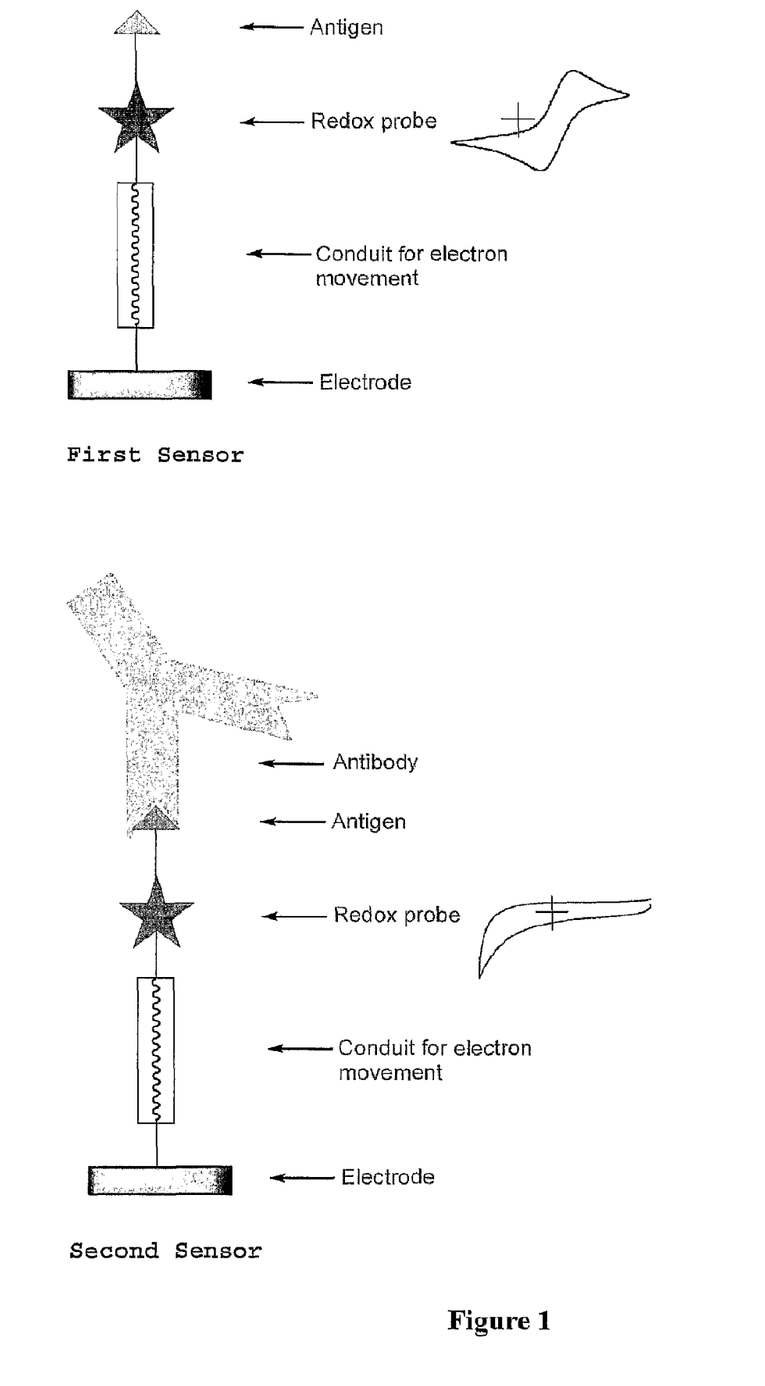
FIG. 1 shows schematic representations of the surfaces of the electrode for two general embodiments of the present invention, together with illustrative cyclic voltammograms.

The present invention can provide a user-intervention-free immunobiosensor which exploits the modulation in the electrochemistry of a redox active species provided as part of the sensor by antibody binding or detachment to/from the sensor. Schematic representations of the surface of an electrode for embodiments of the first and second sensors (labelled "First Sensor" and "Second Sensor" respectively) are shown in FIG. 1. Illustrative cyclic voltammograms for each sensor are depicted beside the respective representation. In FIG. 1, the redox active species is labelled "redox probe". The cyclic voltammograms show the attenuation of the electrochemistry of the redox probe upon the antibody binding to the sensor. It should be noted that the antibody in these representations is depicted for clarity as being approximately only slightly larger than the antigen. The antibody would typically be many times larger than the antigen.

The sensors of the present invention will typically include a large number of redox active species and binding moieties distributed on the surface of the electrode in order for the association of the binding moiety and the analyte to cause a detectable change in the electrochemistry of the redox active species.

The components of the electrochemical sensors of the present invention will now be described in further detail.

Electrodes

Any electrode may be used in the electrochemical sensor of the present invention. Electrodes suitable for use in the sensors of the present invention include, for example, carbon paste electrodes, screen-printed carbon electrodes, glassy carbon (GC) electrodes, gold electrodes, platinum electrodes, carbon nanotube electrodes, indium tin oxide electrodes, silicon electrodes, aluminium electrodes, copper electrodes, etc.

Typically, GC electrodes are used because they are inexpensive and can be mass produced. They are also very dense, chemically inert, electrically conductive and have a relatively well defined structure. GC electrodes can also be modified by the formation of stable self assembled monolayers (SAMs) on the surface of the electrode using techniques described in the art. Modified GC electrodes have a large potential window, which is advantageous because it allows many different types of molecules to be investigated electrochemically (some molecules are not stable at too negative or too positive potentials).

Redox Active Species

The redox active species may be any species that can be electrochemically interrogated. The redox active species must be electrochemically accessible to the electrode in order for electrons to be transferred between the species and the electrode, so that changes in the redox state of the redox active species can be detected by changes in the electrical current through the electrode.

In some embodiments of the first sensor, the binding moiety (e.g. antigen) may itself contain a redox active species. In such embodiments, the sensor need not have an additional redox active centre (i.e. the redox active species is part of the binding moiety).

Similarly, in embodiments of the second sensor where the antibody binding moiety is attached to the sensor via at least part of an antigen, the at least part of an antigen may itself contain a redox active species and the sensor need not have an additional redox active centre.

General examples of suitable redox active species include organometallic complexes, metal ion complexes, organic redox active molecules, metal ions and nanoparticles containing a redox active centre.

Typically, the redox active species is chemically bound to the distal end of a species that is a conduit for electron movement (as will be described below), and therefore bound, via the species that is a conduit for electron movement, to the electrode.

In the sensors of the present invention, the redox active species and the binding moiety are typically situated sufficiently proximate to each other so that the association of the binding moiety with the analyte affects the electrochemistry of the species. For example, the redox active species may be directly bound to the binding moiety. Alternatively, the redox active species may be bound to the binding moiety via a short (e.g. $C_{1-10}$) alkyl chain, or the like. In some embodiments, the redox active species is bound to the binding moiety via a $C_{1-5}$ alkyl chain.

The redox active species in the sensor of the present invention is typically the redox active centre in a redox active compound, where the redox active compound is capable of undergoing chemical reactions in order to bind the redox active centre to other components of the sensor. Compounds that may be used typically have one or more functional groups that enable them to bind to other components of the sensor (e.g. the binding moiety or species that is a conduit for electron movement) via chemical bonds. Preferred redox active compounds that may be used possess amine functional groups, which facilitate the attachment of the compound to other components of the sensor. For example, ferrocenedimethylamine and flavin adenine dinucleotide are redox active compounds that can react with, and be covalently attached to, other compounds via amide coupling(s). The redox active centre in ferrocenedimethylamine is referred to below as the "ferrocene moiety".

Specific examples of compounds that may be used to incorporate the redox active species in the sensor of the present invention include ferrocenedimethylamine, 1,5-diaminonaphthalene, pyrrolo quinoline quinone, 2,3,5,6-tetramethyl-1,4-phenylenediamine, flavin adenine dinucleotide, ethidium, ruthenium$(NH_3)_4$pyridine$^{2+}$, ruthenium(2,2'bipyridyl)$_2$(dipyrido[3,2-$\alpha$-2',3':$\gamma$]phenazine)$^{2+}$, ruthenium((5-glutaric acid monohydride)-1,10-phenanthroline)$_2$(dipyrido[3,2-$\alpha$-2',3':$\gamma$]phenazine)$^{2+}$, ruthenium(2,2'-bipyridyl)$_4$(imidazole)(2-amino-2-deoxyuridine), rhodium(9,10-phenanthrolinequinone diimine)$_2$((5-glutaric acid monohydride)-1,10-phenanthroline)$^{3+}$, rhodium(2,2'-bipyridyl)$_2$(5,6-chrysenequinone diimine)$^{3+}$, osmium(1,10-phenanthroline)$_2$(dipyrido[3,2-$\alpha$-2',3':$\gamma$]phenazine)$^{2+}$, 5,10,12,20-tretrakis(1-methyl-4-)porphyrin, 5,10,12,20-tretrakis(-2-pyridinio)porphyrin, and 3-nitrobenzothiazolo[3,2-$\alpha$] quinoliumchloride.

Electrochemically Accessible to the Electrode

As discussed above, the redox active species must be electrochemically accessible to the electrode in order for changes in the redox state of the species to be detected by changes in the electrical current in the electrode. The redox active species may be held in a position in which it is electrochemically accessible to the electrode by any means, for example, by chemical bonding or by absorption. Typically, the redox active species is bound to the electrode via a species that is a conduit for electron movement. The species that is a conduit for electron movement provides a means by which electrons can move between the redox active species and the electrode, for example by tunneling or electron transport.

Examples of species that can be conduits for electron movement include molecular wires, nanotubes (such as single walled carbon nanotubes) and norbornylogous bridges.

Molecules that may be used to form a conduit for electron movement between the electrode and the redox active species include aliphatic alkanes, oligo(phenylene vinylene), oligo(phenylene ethynylene), polyacetylene, polythiophene, Carotenoids and $Li_2Mo_6Se_6$.

Typically, the species that is a conduit for electron movement is bonded to the surface of the electrode at one of its ends. Typically, the species is substantially linear, and its other end is bonded to the redox active species.

The ends of a compound that can be used to create the species that is a conduit for electron movement in a sensor of the present invention preferably have functional groups (e.g. carboxylic acid functional groups) that are capable of reacting with another compound. Thus, when the compound is bonded to the surface of an electrode via a first reaction (e.g. a coupling reaction), a redox active species possessing an appropriate functional group (e.g. an amine functional group) may be bonded to the compound (and therefore to the electrode) via a second reaction such that the electrode and redox active species are joined by the species that is a conduit for electron movement.

In some embodiments, a combination of one or more different types of species that are conduits for electron movement may be used in the sensor.

Binding Moiety

The binding moiety in the electrochemical sensors of the present invention is capable of associating with the analyte, which results in the electrochemistry of the redox active species being affected. Typically, the association of the binding moiety and analyte is affinity based, that is, the binding moiety and analyte have an affinity for binding to each other. In such cases, the binding typically occurs as a result of the binding moiety or the analyte (the "recognition molecule") having the correct geometric shape for the analyte or the binding moiety to bind whereupon a combination of weak bonding forces, such as hydrogen bonding, van der Waals forces and electrostatic forces, operate cooperatively to strongly bind the analyte and binding moiety together. This is illustrated by antibody-antigen binding events, where variation in up to 17 amino acids in the Fab domains of the antibodies allow an alteration in the geometry of the binding pocket of the antibody as well as the relative balance of binding forces that operate in the binding site.

The sensors of the present invention may be used to detect the presence of any analyte to which the binding moiety is capable of associating (e.g. because of an affinity based binding event).

In addition to antibody/antigen binding events, other affinity based binding events include those between lectins and sugars, peptides and proteins, macrocyclic ligands and organic molecules. The sensors of the present invention can be used to transduce these binding events in order to detect such analytes in a sample, for example, sensors in accordance with the present invention can be used to detect lectins or sugars in a sample, peptides or proteins in a sample, or macrocyclic ligands or organic molecules in a sample. Sensors in accordance with the present invention can, for example, be used to detect one of an antibody/antigen pair (e.g. biotin/antibiotin, endosulfan/antiendosulfan, pollutants such as 2,4-dinitrophenol(DNP)/antiDNP, 2,3,7,8-tetrachlorodibenzofuran (TCBF)/antiTCBF, 2,3,7,8-tetrachloro-dibenzo-p-dioxin (TCDD)/AntiTCDD, 3,3',4,4',5,5'-hexachlorodibiphenyl (HCBP)/antiHCBP, drugs(theophylline/antitheophylline), and pesticides such as atrazine/antiatrazine, and parathion/antiparathion).

If the electrochemical sensor of the present invention is to be used to detect antibodies, the binding moiety is preferably at least part of an antigen to which the antibody is capable of binding.

If the electrochemical sensor of the present invention is to be used to detect antigens, the binding moiety is typically an antibody which is capable of binding to the antigen.

In the first sensor described above, the binding moiety is preferably at least part of an antigen to which the antibody is capable of binding. The binding moiety in the first sensor typically comprises an epitope capable of binding to the antibody. In some embodiments, the binding moiety is the epitope. In embodiments of the first sensor where the binding moiety comprises an epitope, the epitope provides a very high degree of selectivity for the relevant antibody, and the sensor is less susceptible to interference by other species which may be present in the sample to be tested.

In some embodiments, the epitope may be chemically synthesized. That is, the binding moiety may be a chemical analogue of an epitope of the antigen. Alternatively, the epitope may be isolated from the antigen.

The binding moiety in the first sensor is preferably a relatively small species so as not to suppress the electrochemistry of the redox active species when the binding moiety is not bound to the antibody. Thus, in embodiments where the binding moiety is at least part of an antigen to which the antibody is capable of binding, and where the antigen is a small molecule, the antigen itself may be part of the sensor (i.e. the binding moiety is the antigen itself).

The binding moiety in the first sensor is typically situated sufficiently proximate to the redox active species so that the binding of the antibody to the binding moiety affects the electrochemistry of the redox active species. As such, the binding moiety may, for example, be bonded directly to the redox active species. Alternatively, the binding moiety may be bonded to the redox active species via a short length alkyl chain (e.g. $C_{1-10}$) or the like. As noted above, in some embodiments, the redox active species may be part of the binding moiety itself.

In the second sensor described above, the binding moiety is an antibody which is capable of binding to the antigen. Preferably, the second sensor further comprises at least part of an antigen to which the antibody is capable of binding (an "antigen analogue"), and the antibody is releasably attached to the sensor because it is releasably bound to the antigen analogue. The antigen analogue in the second sensor may be the same as the examples of the "binding moiety" discussed above in relation to the first sensor.

The antigen analogue is typically a relatively small species so that the electrochemistry of the redox active species is less suppressed when the antibody detaches from the sensor than when the antibody is bound to the antigen analogue.

In order for the antibody binding moiety in these embodiments of the second sensor to be situated sufficiently proximate to the redox active species such that detachment of the antibody from the sensor affects the electrochemistry of the redox active species, the antigen analogue may, for example, be bonded directly to the redox active species. Alternatively, the antigen analogue may be bonded to the redox active species via a short length alkyl chain or the like.

Formation of Electrochemical Sensors

The chemistry and processes relating to the formation of self assembled monolayers (SAMs) on the surface of an electrode is well-known.

A process for forming on a GC electrode a self assembled monolayer comprising a redox active species and a binding moiety will now be described to illustrate how a sensor in accordance with a preferred embodiment of the present invention can be prepared. Monolayers may be formed on the surface of other types of electrode using techniques well known in the art.

Using techniques known in the art, a species that is a conduit for electron movement can be bound to the surface of a GC electrode by the electrochemical reduction at the electrode of an aryl diazonium salt that is substituted with the species. A negative potential at the electrode causes the diazonium salt to reduce (with the release of $N_2$), which produces a radical on the aryl ring of the diazonium salt. Radical attack on the GC electrode surface results in the formation of a C—C bond between the electrode and the aryl ring to give a stable SAM.

Figure 2:
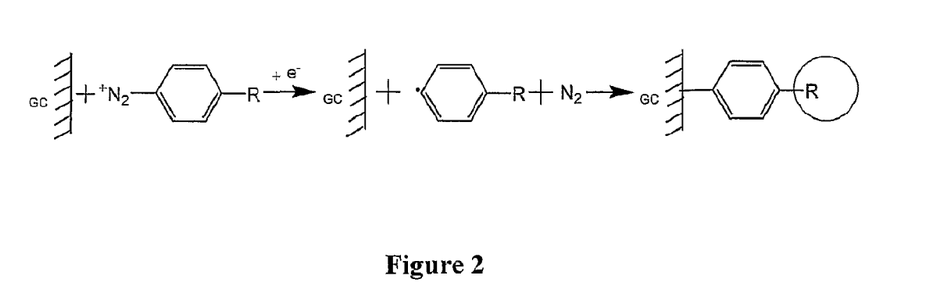
FIG. 2 shows the reaction scheme for the electrochemical reduction of a substituted aryl diazonium salt onto the surface of a GC electrode.

When the species is bound to the 4-position of the aryl group, the species projects outwards in an approximately normal conformation from the surface of the electrode in the resultant monolayer. The reaction scheme for the electrochemical reduction of a 4-substituted aryl diazonium salt is depicted in FIG. 2. In FIG. 2, the substituent R is the substituent on the aryl diazonium salt, and may be a species that is a conduit for electron movement.

Alternatively, a GC electrode may be modified with an aryl diazonium salt having a functional group capable of undergoing subsequent reactions at the 4-position of the aryl group. A species that is a conduit for electron movement may then be bonded to the 4-position of the aryl group (and hence the electrode) in a reaction subsequent to the reaction in which the aryl diazonium salt is reduced onto the surface of the electrode.

Typically, the SAM formed on the surface of the GC electrode includes a mixture of species that are a conduit for electron movement and one or more kinds of blocking agents (sometimes referred to below as "insulators"). The blocking agents effectively "insulate" the remainder of the surface of the electrode by preventing any species which may be present in the sample to be tested from adsorbing on to the electrode. The risk of such interactions interfering with the detection of the analyte (e.g. the antibody or antigen) in the sample is therefore lessened, which gives a more reliable sensor.

In some embodiments, the non-specific adsorption of molecules on the surface of the electrode may be minimized by masking the surface of the electrode with blocking agents such as bovine serum albumin or a hydrophilic layer formed by a compound such as polyethylene glycol (PEG). PEG comprises short chain ethylene oxide polymers that may be bound to the 4-position of some of the aryl groups attached to the surface of the GC electrode.

The proportion of species that are a conduit for electron movement to insulator on the SAM may, for example, be about 1:1, 1:10, 1:20, 1:50, 1:100 or 1:1000.

The distal end of the species that is a conduit for electron movement may be provided with a functional group (e.g. a carboxylic acid functional group) that is capable of reacting with another compound. Thus, when the species that is a conduit for electron movement has been bonded to the surface of the GC electrode to form a SAM as described above, a compound comprising a redox active species and possessing an appropriate functional group (e.g. an amine functional group in the case of ferrocenedimethylamine or flavin adenine dinucleotide) may be bonded to the distal end of the species (and therefore to the electrode) via a coupling reaction. Other functional groups could, of course, be utilized to enable the species that is a conduit for electron movement and a compound containing the redox active species to be joined using standard chemical techniques.

The binding moiety may then be bound to the redox active species. For example, one of the amine groups of ferrocenedimethylamine may be used to couple the ferrocene moiety to the distal end of the species that is a conduit for electron movement, and the other amine group may be used to couple the binding moiety to the ferrocene moiety. In these circumstances, the ferrocene moiety joins and bridges the species that is a conduit for electron movement and the binding moiety.

The binding moiety may alternatively be bonded to the redox active species via a short length alkyl chain, or the like.

In some embodiments, another species may be bound to the redox active species, and the binding moiety then bound to that species. For example, in some embodiments, an antigen analogue may be bonded directly to the redox active species, or bonded to the redox active species via a short length alkyl chain, or the like, and the binding moiety (an antibody) may then be bound to the antigen analogue by exposing the antigen analogue to the antibody under conditions that allow the antibody to bind to the antigen analogue.

Figure 3:
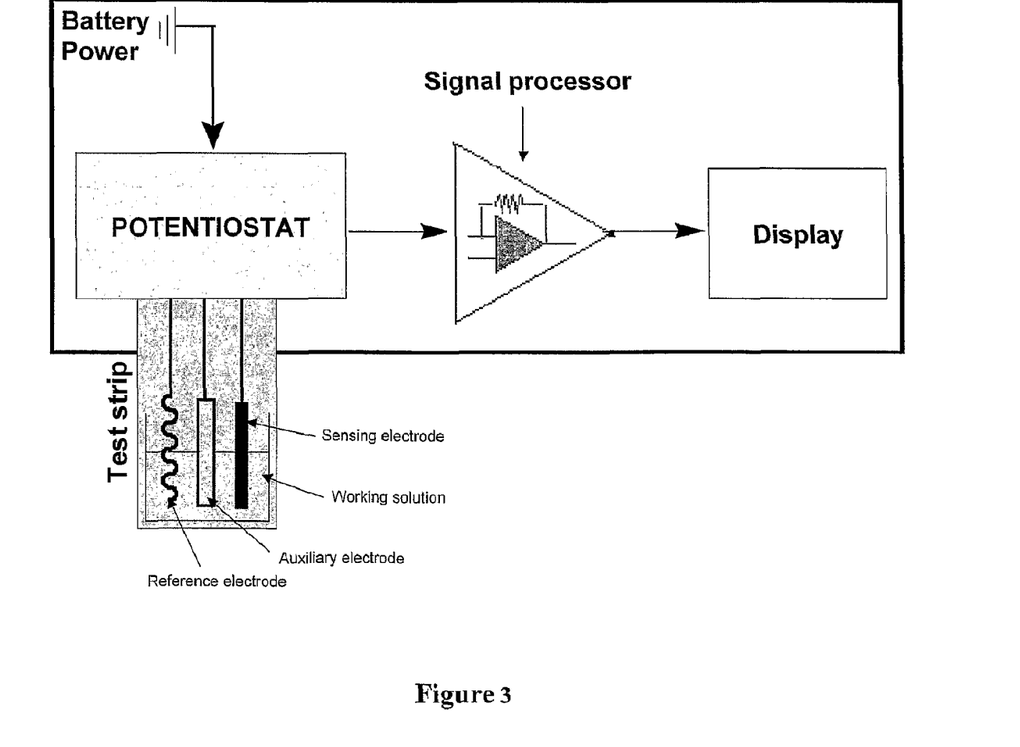
FIG. 3 shows a schematic representation of an embodiment of the electrochemical sensor of the present invention.

The amperometric sensors of the present invention will of course typically include additional components that enable the results of the sample analysis to be viewed by the operator. For example, the sensor would typically include a source of electricity (such as a battery), a potentiostat, a signal processor and a display. The electrode having the SAM described above would typically be provided as part of a test strip comprising the electrode having the SAM described above, a reference electrode and an auxiliary electrode. A schematic representation of such a sensor is depicted in FIG. 3. In use, the test strip would be exposed to the test sample (e.g. a body of water, a patient's blood, a foodstuff, a drink, or an industrial or household waste sample).

It is envisaged that an electrode of the present invention could be incorporated into existing sensors for detecting the presence of an analyte in a sample to provide a sensor of the present invention.

Preferred Embodiments of the Electrochemical Sensors

Figure 4:
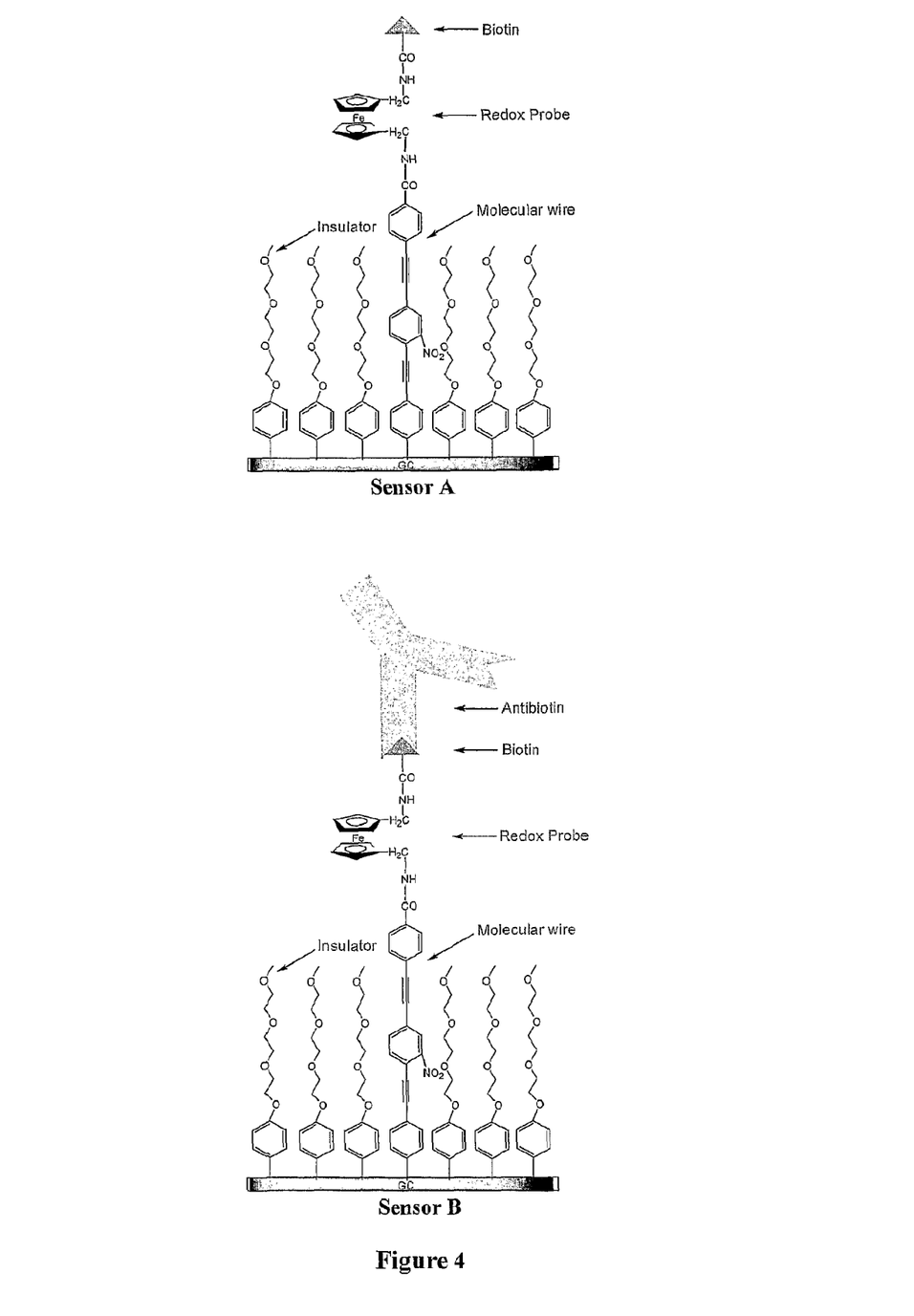
FIG. 4 shows schematic representations of the surfaces of the electrode for two embodiments of the present invention.

Schematic representations of the surfaces of the electrode of two specific embodiments of the first and second sensors are depicted in FIG. 4 (labelled "Sensor A" and "Sensor B" respectively). In these sensors, the electrodes are GC electrodes and the redox active species is a ferrocene moiety. The GC electrodes have a SAM consisting of a molecular wire in the form of oligo(phenylethylene) and an "insulator" in the form of PEG chains, both of which are bonded to the 4-position of an aryl group bonded to the electrode.

In Sensor A, the redox probe is a ferrocene moiety and is bonded to and bridges the distal end of the molecular wire and the binding moiety which is biotin (an antigen).

Sensor B includes the same electrode, SAM and redox probe, and also includes at least part of an antigen in the form of biotin. As is the case in Sensor A, the biotin in Sensor B is bound to the ferrocene moiety. In Sensor B, the binding moiety is antibiotin, which is bound to the biotin.

Sensors A and B are essentially the same, however, the antibiotin is bound to the biotin in Sensor B. Sensor A can readily be converted into Sensor B simply by exposing Sensor A to a sample containing antibiotin. Similarly, Sensor B can be converted into Sensor A by exposing Sensor B to a sample containing biotin.

The molecular wire, having the ferrocene moiety bonded to one end and the electrode bonded to its other end, enables the transduction of the biorecognition event to be transferred to the electrode. The molecular wire transfers electrons rapidly and efficiently between the ferrocene moiety and the electrode.

Sensor A can be used to detect the presence of antibiotin in a sample by taking electrochemical measurements which indicate whether there is a change in the electrochemistry of the ferrocene moiety as a result of the antibiotin binding to the biotin, as will now be described The electrode of Sensor A is immersed for 20 mins in a test sample. During this time, if there is any antibiotin in the sample, at least some of the antibiotin will bond to the biotin on the sensor, resulting in the electrochemistry of the ferrocene moiety being suppressed. This decrease in electrochemistry is detectable and can be quantified using electrochemical techniques well known in the art.

Sensor B can be used to detect the presence of the antigen (i.e. biotin) in a sample by taking electrochemical measurements which indicate whether there is a change in the electrochemistry of the ferrocene moiety as a result of the antibiotin disassociating from the biotin bound to the sensor, as will now be described.

The electrode of Sensor B is immersed for 20 mins in a test sample. During this time, if there is any biotin in the sample, at least some of the antibiotin bonded to the biotin in the sensor will detach from the biotin in the sensor and bond to the free biotin in the sample.

As a result of the antibiotin detaching from the sensor, the electrochemistry of the ferrocene moiety will increase because it is no longer engulfed by the antibiotin and ions may now interact with it. This increase in electrochemistry is detectable and can be quantified using electrochemical techniques well known in the art.

Detecting and Quantifying the Electrochemistry of the Redox Active Species

The association of the analyte with the binding moiety (e.g. the binding of the antibody to the binding moiety in the first sensor, or the disassociation of the antibody from the second sensor when the antibody binding moiety binds to antigens in the sample) affects the electrochemistry of the redox active species, and thus causes an alteration in the ability of the electrode to oxidise and reduce the redox active species. For example, upon sweeping the potential of the electrode of a sensor of the present invention progressively more positive (cyclic voltammetry), or stepping the potential progressively more positive (Osteryoung square wave voltammetry), the redox active species becomes more susceptible to oxidation and eventually oxidises (e.g. a ferrocene moiety will be oxidised to the ferrocinium ion). In the voltammograms, this is represented by an increase in anodic current as electrons transfer to the electrode. Sweeping the potential back more negatively will result in the reduction of the redox active species (e.g. the reduction of the ferrocinium ion to the ferrocene moiety) as electrons transfer from the electrode to the redox active species. The association of the binding moiety with the analyte (for example, in the first sensor, the binding of the antibody to the binding moiety) will affect the ability of the electron transfer to occur, increasing or diminishing the peaks observed in the voltammograms.

It is also possible to quantify the amount of analyte present in a sample using the electrochemical sensors of the present invention. For example, interaction between the first sensor and the complementary antibody results in the antibody binding to the binding moiety. The formed bulky structure of the binding moiety/antibody biomolecular pair perturbs the electrical communication between the redox active species and the sample, and the resulting amperometric signal is inhibited. The extent of the electrode coverage by the antibody is proportional to the antibody concentration in the sample and to the time for which the electrode is exposed to the sample. Thus, if the duration of exposure to the sample is fixed, the decrease in the electrode amperometric response correlates with the antibody concentration in the sample.

EXAMPLES

Reagents and Materials

Tetrabutylammonium tetrafluoroborate ($NBu_4BF_4$), sodium tetrafluoroborate ($NaBF_4$), para-aminobenzoic acid, aniline, 4-mercaptobenzoic acid, 1-propanethiol, ferricyanide ($K_4Fe(CN)_6$), 1,3-Dicyclohexylcarbodiimide (DCC), ferrocenecarboxaldehyde, sodium cyanoborohydride, acetonitrile ($CH_3CN$, HPLC grade), and absolute ethanol were obtained from Sigma Chem. Co. (Sydney, Australia). Sulfo-NHS-Biotin was purchased from Pierce Chemical Company. Anti-biotin from goat, bovine serum albumin fraction V (BSA), anti-pig IgG and free biotin were purchased from Sigma. Reagent grade dipotassium orthophosphate, potassium dihydrogen orthophosphate, potassium chloride, sodium hydroxide, sodium chloride, sodium nitrite, ammonium acetate, sulphuric acid, hydrochloric acid, methanol and diethyl ether were purchased from Ajax Chemicals Pty. Ltd. (Sydney, Australia). Single walled carbon nanotubes were obtained from Carbon Nanotechnologies Inc, USA. All reagents were used as received, and aqueous solutions were prepared with purified water (18 $M\Omega cm^{-1}$, Millipore, Sydney, Australia).

The phosphate buffered saline (PBS) solutions described below were 0.15 M NaCl and 0.1 M $K_2HPO_4/KH_2PO_4$ and adjusted with NaOH or HCl solution to pH 7.3. The phosphate buffer solutions described below were 0.05 M KCl and 0.05 M $K_2HPO_4/K_1H_2PO_4$ and adjusted with NaOH or HCl solution to pH 7.0.

Electrochemical Measurements

All electrochemical measurements were performed with a BAS-100B electrochemical analyser (Bioanalytical System Inc., USA) and a conventional three-electrode system. GC electrodes (Bioanalytical Systems Inc., USA) were prepared from 3 mm-diameter rods embodied into epoxy resin and were used as working electrodes. Platinum foil and an Ag/AgCl (3.0 M NaCl) electrode were used as the counter (auxiliary) and reference electrodes respectively. All potentials are reported versus the Ag/AgCl reference electrode at room temperature. All CV measurements were carried out in pH 7.0 phosphate buffer.

Example 1

Formation of an Electrochemical Sensor

Modification of GC electrodes with molecular wire (MW) and polyethylene glycol (PEG)

GC electrodes were polished successively in 1.0, 0.3, and 0.05 micron alumina slurries made from dry Buehler alumina and Milli-Q water on microcloth pads (Buehler, Lake Bluff, Ill., USA). The electrodes were thoroughly rinsed with Milli-Q water and sonicated in Milli-Q water for 5 min between polishing steps. Before derivatization, the electrodes were dried in an argon gas stream.

Surface derivatization of the GC electrodes was carried out in an acetonitrile solution of 1 mM aryl diazonium salt solution and 0.1 M $NaBu_4BF_4$ using cyclic voltammetry (CV) with a scan rate of 100 mV $s^{-1}$ for two cycles between +1.0 V and −1.2 V. The diazonium salt solution contained a mixture of diazonium molecules substituted at the 4-position by molecular wire molecules (MW) and PEG molecules in a molar ratio of 1:20. The MW used were prepared from methyl 2'-nitro-4,4'-diphenylethenyl-4"-benzoic acid benzenediazonium tetrafluoroborate using the methods disclosed by Tour and co-workers (Chem. Eur. J. 2001, 7, 5118-5134; Organic Letters 2001, 3, 993-995). The diazonium salt solution was deaerated with argon for at least 15 min prior to derivatization.

The surfaces of the resultant electrodes have a SAM comprising the MW molecules and the "insulating" PEG molecules bound to the surface via the aryl group. The proportion of MW:PEG molecules on the SAM was about 1:20.

These electrodes were rinsed with copious amounts of acetonitrile and then water, and dried under a stream of argon prior to the next step.

Covalent Coupling of Ferrocenedimethylamine to the Molecular Wire Molecules on the Modified GC Electrode Covalent attachment of ferrocenedimethylamine to the carboxylic acid terminated molecular wire molecules on the surface of the modified electrode was achieved by dipping the electrode into an absolute ethanol solution containing of 40 mM of 1,3-dicyclohexylcarbodiimide (DCC) and 5 mM ferrocenedimethylamine overnight.

Immobilization of Biotin and Anti-Biotin on the Modified GC Electrode

After the ferrocenedimethylamine was coupled to the MW via the first amine group of ferrocenedimethylamine, the other amine group remained available for bonding. The modified GC electrode of the previous step was immersed in a 1 mg $mL^{-1}$ solution of NHS-biotin (NHS-biotin is a biotin molecule modified so it has a functional group that is susceptible to nucleophilic attack from amine groups) in PBS (pH 7.3) for 2 h at 4° C. in order to bond the NHS-biotin to the free terminal amines of the surface bound ferrocene moieties. The resultant electrode may be used in an embodiment of the sensor A described above.

The electrode was then rinsed with copious amounts of water and PBS, and immersed into a solution containing 0.5 µM anti-biotin (the antibody of biotin) dissolved in PBS for 20 min at 4° C. The antibiotin bound to and remained bonded to the biotin labelled GC electrode because of the strong affinity between the biotin/antibiotin biomolecular pair. The resultant electrode may be used in an embodiment of the sensor B described above.

Example 2

Detecting the Attachment and Detachment of Antibiotin

Electrochemistry of the Sensor after Immobilization of Biotin and its Antibody

Figure 5:
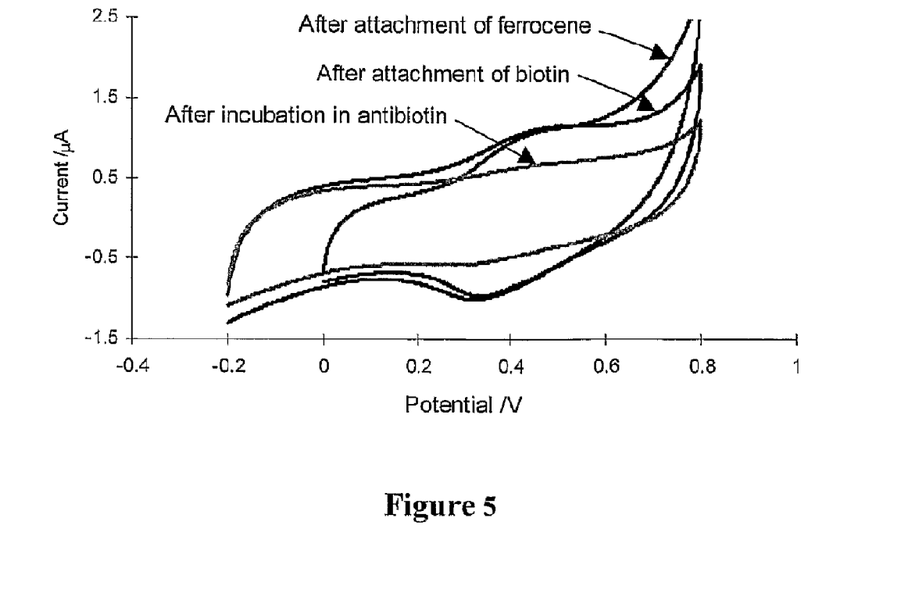
FIG. 5 shows overlaid cyclic voltammograms of modified GC electrodes having a SAM comprising molecular wire molecules and PEG molecules after the step-wise attachment of (i) ferrocenedimethylamine, (ii) biotin, and (iii) antibiotin in 0.05 M phosphate buffer (0.05 M KCl, pH 7.0) at a scan rate of 100 mV s$^{-1}$.

FIG. 5 shows the cyclic voltammograms (CVs) of the modified GC electrodes described in Example 1 after the step-wise attachment of (i) ferrocenedimethylamine, (ii) biotin, and (iii) antibiotin in 0.05 M phosphate buffer (0.05 M KCl, pH 7.0) at a scan rate of 100 mV $s^{-1}$.

After the biotin was bonded to the ferrocene moiety, the CV of the modified GC electrode did not change significantly.

However, after the sensor was immersed in the solution containing antibiotin, the CV of the GC electrode demonstrated a pronounced reduction in peak currents. These results are consistent with antibiotin binding to the biotin and enfolding the ferrocene molecule, thereby restricting ions from interacting with the ferrocene such that the redox activity of the ferrocene is suppressed.

Figure 6:
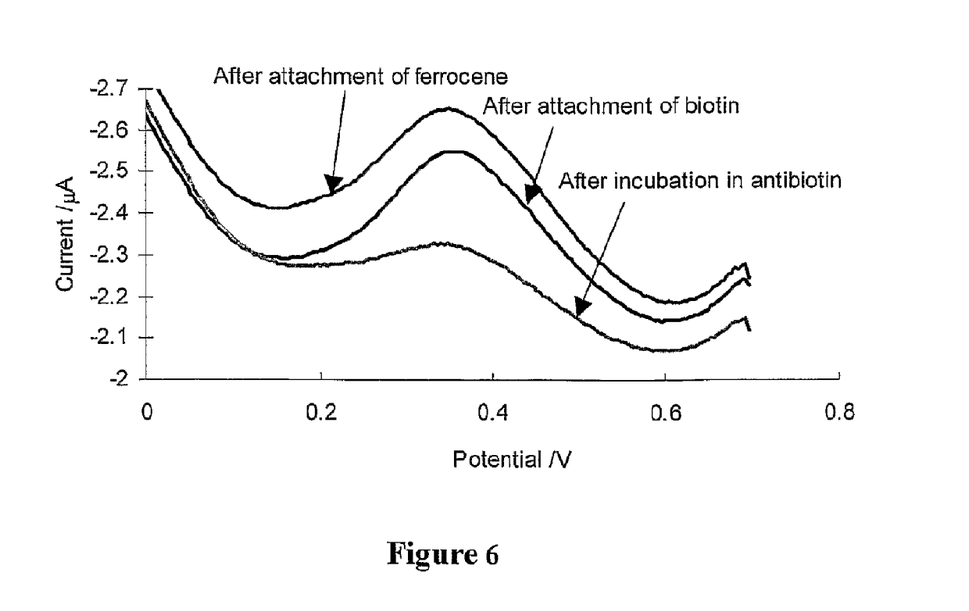
FIG. 6 shows overlaid OSWV of the modified GC electrodes used to produce the cyclic voltammograms shown in FIG. 5 in 0.05 M phosphate buffer (0.05 M KCl, pH 7.0) at a scan rate of 100 mV s$^{-1}$.

As can be seen from FIG. 6, OSW voltammograms (which are a more sensitive electrochemical technique) of the same modified GC electrodes also demonstrated a pronounced reduction in peak currents after incubation with anti-biotin.

Control experiments under similar conditions to those described above show that no redox peaks are observed if ferrocenedimethylamine is replaced by ethylenediamine in the sensors described in Example 1. This indicates that a redox active species is an essential component of the sensors of the present invention.

Further, CV experiments under similar conditions to those described above, but using electrodes on which the NHS-biotin has not been bonded to the ferrocene, show almost no change in peak current when those electrodes are exposed to a sample containing antibiotin. This indicates that the presence of antibiotin in a sample does not itself suppress the electrochemistry of the ferrocene moiety.

The specificity of the sensor described above is demonstrated in that almost no decrease in current density was observed upon treatment of the sensor A described in Example 1 (i.e. the sensor with no antibiotin bound to the biotin) with other proteins, such as BSA and anti-pig IgG, under identical conditions. These results indicate that the antibiotin specifically binds to the biotin molecules on the sensor.

The non-specific adsorption of other proteins on the electrode's surfaces was also assessed by incubating the sensor A described in Example 1 with a solution containing BSA and anti-pig IgG. Since these two proteins are not specific for NHS-biotin and will therefore not become attached to the biotin (as was confirmed by the experiments described in the previous paragraph), any current decrease would be indicative of non-specific adsorption of the proteins onto the surface of the electrode. However, these experiments have shown that there is a very small current decrease, indicating that only 0.1% of the current decrease was due to non-specific adsorption of protein.

Example 3

Quantification of the Concentration of Anti-Biotin in a Sample

To determine the sensitivity of the sensor A of Example 1 for detecting an antibody, the sensor was tested using samples containing different concentrations of antibiotin.

Figure 7:
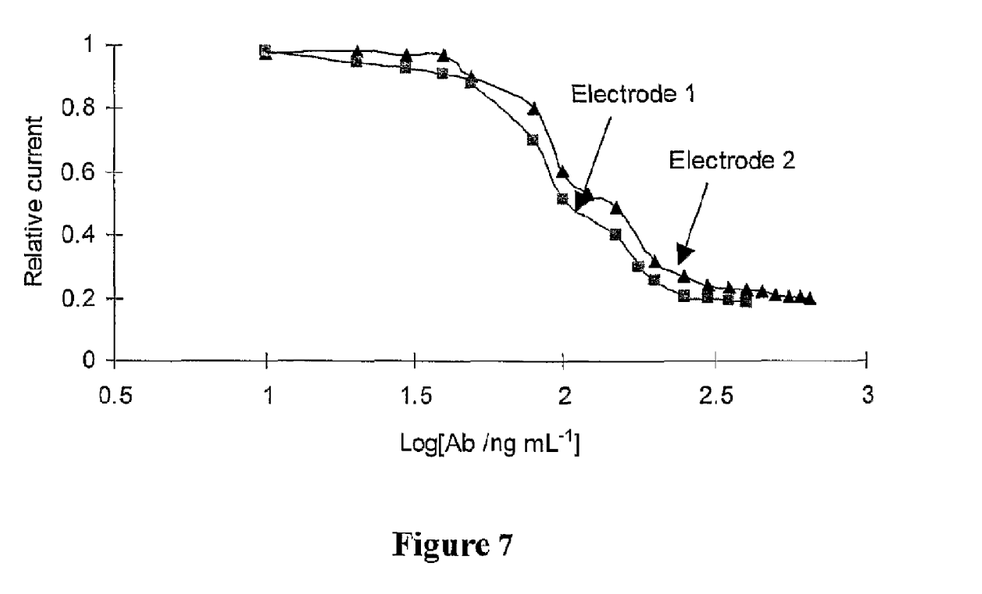
FIG. 7 shows a calibration plot for an experiment in which two similar electrochemical sensors in accordance with an embodiment of the present invention are used to detect antibiotin in a sample. The plot shows the relative current (obtained by dividing the current before incubating the sensors with antibiotin by the current after incubation) versus the logarithm of the antibiotin concentration.

Immersion of the electrode into a buffer solution with stepwise addition of antibiotin between ~5 to 500 ng mL$^{-1}$ resulted in a stepwise decrease in the OSWV peak current of the ferrocene molecule. FIG. 7 shows the calibration curve for the detection of antibiotin using two similar electrodes (labelled "Electrode 1" and "Electrode 2") prepared as described in Example 1. The lowest detected concentration of antibiotin was 5 ng mL$^{-1}$ (i.e. ~5 ppb)

The response of a number of other electrodes made using the same techniques was very similar; hence construction of the electrodes is reproducible. Nine electrodes for immunosensors were prepared by following identical steps (the results for two of these sensors are shown in FIG. 7) and their response toward antibiotin led to a relative standard deviation of only 6%.

Example 4

Displacement Assay

The reversibility of the sensor B of Example 1 was demonstrated by adding free biotin to a sample in which sensor B was immersed.

Figure 8:
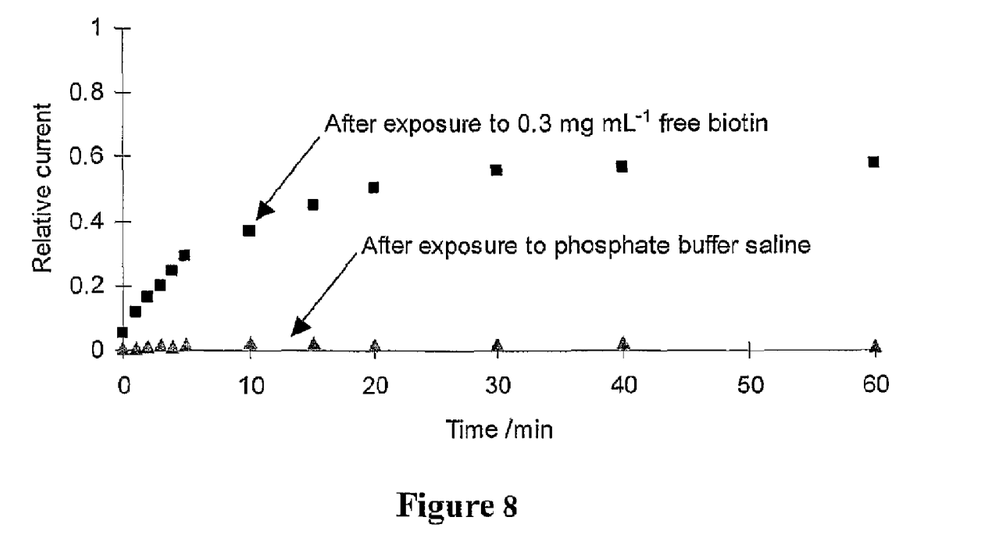
FIG. 8 shows a graph of the relative current (obtained by dividing the current before the sensor is incubated in a sample containing 0.3 mg mL$^{-1}$ free biotin by the current after incubation) versus time for a sensor in accordance with an embodiment of the present invention. The graph also shows the results of a control experiment in which the same sensor was exposed to phosphate buffer containing no biotin.

The relative current (obtained by dividing the current before the sensor was exposed to the sample by the current after exposure) versus time is shown in FIG. 8. As shown in FIG. 8, an increase in current density was observed upon the addition of free biotin, which is consistent with the displacement of antibiotin from the sensor. In a control experiment, the same sensor was left in the phosphate buffer solution but free biotin was not added. As can be seen, no increase in current density was observed with time, which is consistent with the antibiotin remaining bound to the biotin and attached to the sensor.

Example 5

Quantification of the Concentration of Biotin in a Sample

Figure 9:
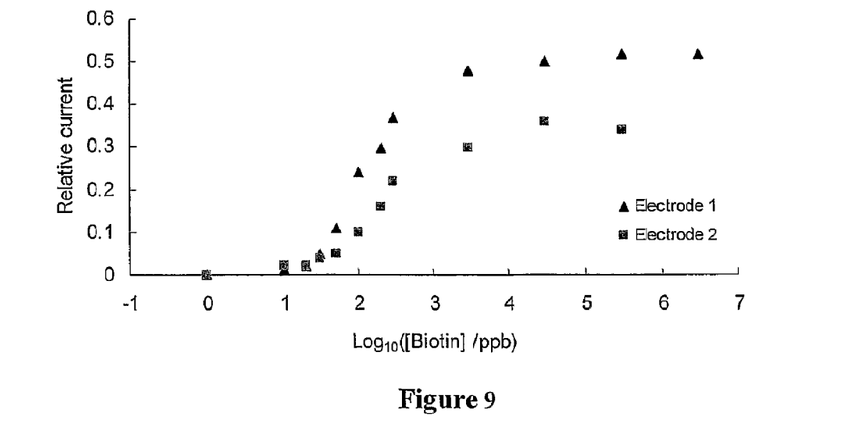
FIG. 9 shows a calibration plot for an experiment in which two similar electrochemical sensors in accordance with an embodiment of the present invention are used to detect biotin in a sample. The plot shows the relative current (obtained by dividing the current before incubating the sensors with biotin by the current after incubation) versus the logarithm of the biotin concentration.

To determine the sensitivity of the sensor B of Example 1 for detecting an antigen, the sensor was tested using samples containing different concentrations of biotin. Immersion of the electrode into a buffer solution with stepwise addition of biotin between ~30 ng mL$^{-1}$ to 0.3 mg mL$^{-1}$ resulted in a stepwise increase in the OSWV peak current of the ferrocene molecule. FIG. 9 shows the calibration curve for the detection of biotin using two similar electrodes (labeled "Electrode 1" and "Electrode 2") prepared as described in Example 1. The lowest detected concentration of biotin was 30 ng mL$^{-1}$ (i.e. 30 ppb)

Example 6

Using a Carbon Nanotube as the Conduit for Electron Transfer

Experiments in which the molecular wire used in the sensors of Examples 1-5 was replace with a single walled carbon nanotubes (SWNTs) are now described.

Cutting of the SWNTs

An initial step requires the carbon nanotubes to be shortened into manageable lengths. The shortening process was performed by weighing 10 mg of pristine SWNT into a 250 mL flat bottom flask containing 40 mL of a 3:1 v/v solution of concentrated sulfuric acid (98%) and concentrated nitric acid (70%), and sonicated in a water bath at 35-40° C. for 4 hours.

The resultant suspension was then diluted to 200 mL with water. The cut SWNTs were collected on a 220 nm pore filter membrane (type: Millipore) and washed with 10 mM NaOH aqueous solution, followed by Milli-Q water until the pH of the filtrate reached 7.0. The cut SWNTs were dispersed in DMF and formed a very good suspension without any aid of surfactant. The cutting process results in carboxylic acid moieties being present on the ends of the carbon nanotubes.

Modification of Glassy Carbon Electrodes with Aligned SWNTs

The modification of glassy carbon electrodes with aligned SWNTs first requires the glassy carbon electrode to be modified with an amine terminated SAM. This amine terminated SAM was produced via the reductive adsorption of 4-aminophenyl diazonium salt onto the electrode surface as described in Example 1. The SWNTs are covalently attached to the 4-aminophenyl modified glassy carbon electrode by dispersing the cut SWNT (0.2 mg) in 1 mL of dimethylformamide (DMF) with 0.5 mg of dicyclohexyl carbodiimide (DCC). DCC converts the carboxylic acid group at the end of the shortened SWNTs into an active carbodiimide ester. The 4-aminophenyl modified GC electrode was then placed in the SWNT solution for 6 hours, during which the amine at the terminus of the monolayer on GC surfaces forms an amide bond with one end of each nanotube. Ferrocene dimethylamine and NHS-biotin were subsequently attached to the ends of the SWNTs in the same manner to that described in Example 1.

Detecting Antibiotin Using SWNTs as the Conduit for Electron Transfer

Figure 10:
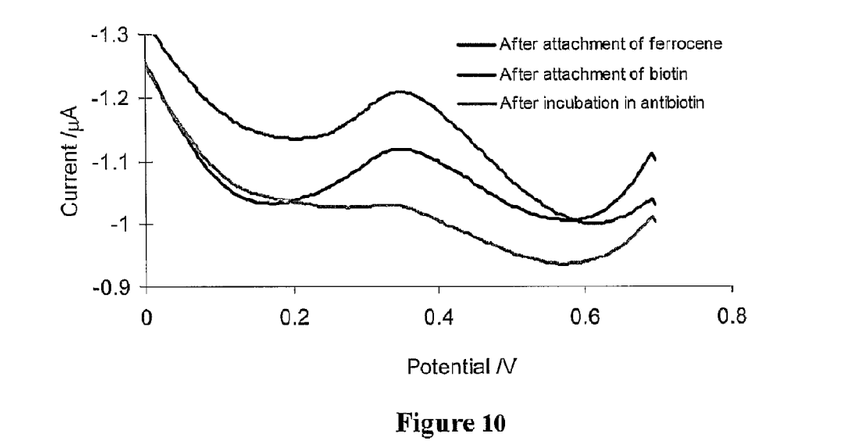
FIG. 10 shows overlaid OSWV of modified GC electrodes having a SAM comprising single-walled carbon nanotubes and PEG molecules after the step-wise attachment of (i) ferrocenedimethylamine, (ii) biotin, and (iii) antibiotin in 0.05 M phosphate buffer (0.05 M KCl, pH 7.0)

FIG. 10 shows the OSWVs of the modified GC electrodes described above after the step-wise attachment of (i) ferrocenedimethylamine, (ii) biotin, and (iii) antibiotin in 0.05 M phosphate buffer (0.05 M KCl, pH 7.0). As can be seen, these results are very similar to those shown in FIG. 6 (described in Example 2), which indicates that electrochemical sensors having SWNTs as conduits for electron transfer operate in a consistent manner to electrochemical sensors having molecular wires as conduits for electron transfer.

Figure 11:
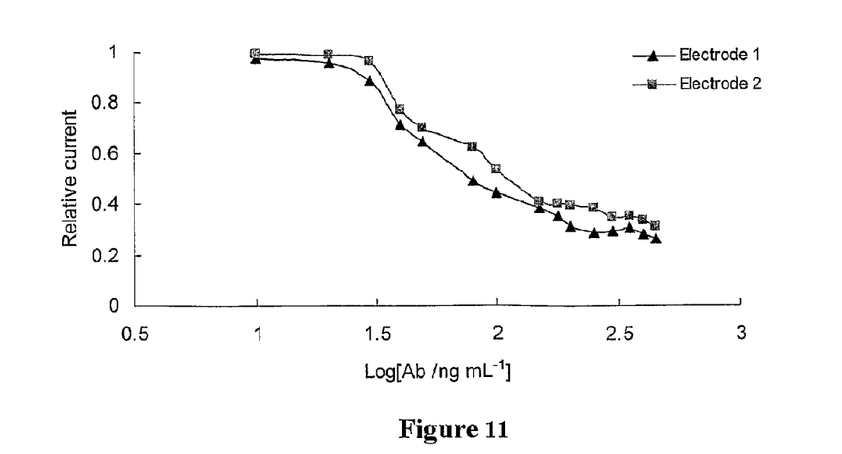
FIG. 11 shows a calibration plot for an experiment in which two similar electrochemical sensors (having a SAM comprising single-walled carbon nanotubes) in accordance with an embodiment of the present invention are used to detect antibiotin in a sample. The plot shows the relative current (obtained by dividing the current before incubating the sensors with antibiotin by the current after incubation) versus the logarithm of the antibiotin concentration.

Quantification of the Concentration of Antibiotin in a Sample when a SWNT is Used as the Conduit for Electron Transfer To determine the sensitivity of the sensor described above (i.e. in which the conduit for electron transfer is a SWNT) for detecting antibiotin, the sensor was tested using samples containing different concentrations of antibiotin. Immersion of the electrode into a buffer solution with stepwise addition of antibiotin between ~10 ng mL$^{-1}$ to 500 ng mL$^{-1}$ resulted in a stepwise decrease in the OSWV peak current of the ferrocene molecule. FIG. 11 shows the calibration curve for the detection of antibiotin using two similar electrodes (labeled "Electrode 1" and "Electrode 2") prepared as described above. The lowest detected concentration of antibiotin was 10 ng mL$^{-1}$ (i.e. 10 ppb).

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. An amperometric electrochemical sensor for detecting an analyte, the sensor comprising:
an electrode;
a redox active species that is bound to the electrode by a species that is a conduit for electron movement and is electrochemically accessible to the electrode; and
a binding moiety capable of associating with the analyte;
wherein the association of the binding moiety with the analyte affects the electrochemistry of the redox active species.

2. The electrochemical sensor as claimed in claim 1, wherein the analyte is an antibody, and wherein:
the binding moiety is capable of becoming bound to the antibody; and
wherein binding of the antibody to the binding moiety affects the electrochemistry of the redox active species.

3. The sensor as claimed in claim 2, wherein the binding moiety is at least part of an antigen.

4. The sensor as claimed in claim 3, wherein the binding moiety comprises an epitope capable of becoming bound to the antibody.

5. The sensor as claimed in claim 4, wherein the binding moiety consists of the epitope.

6. The sensor as claimed in claim 4, wherein the epitope is chemically synthesised.

7. The sensor as claimed in claim 3, wherein the binding moiety consists of an antigen to which the antibody binds.

8. The sensor as claimed in claim 2, wherein the binding moiety is bound to the redox active species.

9. The sensor as claimed in claim 2, wherein the binding moiety is at least part of biotin or endosulfan.

10. The electrochemical sensor as claimed in claim 1, wherein the analyte is an antigen, and wherein:
the binding moiety is an antibody capable of binding to the antigen; and
wherein detachment of the antibody from the sensor affects the electrochemistry of the redox active species.

11. The sensor as claimed in claim 10, which further comprises at least part of an antigen, wherein the binding moiety is bound to the at least part of an antigen.

12. The sensor as claimed in claim 11, wherein the at least part of an antigen comprises an epitope of the antigen.

13. The sensor as claimed in claim 11, wherein the at least part of an antigen is bound to the redox active species.

14. The sensor as claimed in claim 10, wherein the binding moiety is an anti-biotin or antiendosulfan antibody.

15. The sensor as claimed in claim 1, wherein the species that is a conduit for electron movement is a molecular wire or a nanotube.

16. The sensor as claimed in claim 1, wherein the redox active species is a ferrocene moiety.

17. The sensor as claimed in claim 1, wherein the electrode is a glassy carbon electrode.

18. The sensor as claimed in claim 1, which Further comprises blocking agents bound to the electrode.

19. The sensor as claimed in claim 18, wherein the blocking agents are polyethylene glycol moieties.

20. The sensor as claimed in claim 1, further comprising a detector capable of detecting changes in the electrochemistry of the redox active species as a result of the association of the binding moiety with the analyte.

21. The sensor as claimed in claim 1, further comprising an electrical power source and a display for displaying electrochemical readings from the electrode.

22. A method for detecting the presence of an analyte in a sample, the method comprising the steps of:
exposing to the sample the electrochemical sensor of claim 1; and
taking amperometric electrochemical measurements which indicate whether there is a change in the electrochemistry of the redox active species as a result of association of the binding moiety with the analyte.

23. A method for detecting the presence of an analyte in a sample, the method comprising the steps of:
exposing to the sample a binding moiety capable of becoming associated with the analyte, the binding moiety being associated with a redox active species that is bound to the electrode by a species that is a conduit for electron movement and is electrochemically accessible to the electrode; and
taking amperometric electrochemical measurements which indicate whether there is a change in the electrochemistry of the redox active species as a result of association of the binding moiety with the analyte.

24. The method as claimed in claim 23, wherein the analyte is an antibody and wherein the binding moiety is capable of becoming bound to the antibody, the method further comprising the step of:
taking electrochemical measurements which indicate whether there is a change in the electrochemistry of the redox active species as a result of the antibody binding to the binding moiety.

25. The method as claimed in claim 24, wherein the binding moiety is bound to the redox active species.

26. The method as claimed in claim 24, wherein the binding moiety, redox active species and electrode are part of an electrochemical sensor.

27. The method as claimed in claim 23, wherein the analyte is an antigen and wherein the binding moiety is an antibody capable of binding to the antigen, the method further comprising the step of:
taking electrochemical measurements which indicate whether there is a change in the electrochemistry of the redox active species as a result of the binding moiety disassociating from the redox active species.

28. The method as claimed in claim 27, wherein the binding moiety is attached to the redox active species via at least part of an antigen to which the antibody is capable of binding.

29. The method as claimed in claim 27, wherein the binding moiety, redox active species and electrode are part of an electrochemical sensor.

30. The method as claimed in claim 23, wherein the electrochemical measurements are taken during association of the binding moiety with the analyte.

31. An electrode, wherein a redox active species is bound to the surface of the electrode by a species that is a conduit for electron movement and a binding moiety capable of associating with an analyte is associated with the redox active species, and wherein association of the binding moiety with the analyte affects the electrochemistry of the redox active species and is detectable by amperometric electrochemical measurements.

32. The electrode as claimed in claim 31, wherein the binding moiety is bound to the redox active species.

33. The electrode as claimed in claim 31, wherein the analyte is an antibody, and the binding moiety comprises at least part of an antigen.

34. The electrode as claimed in claim 31, wherein the analyte is an antigen and the binding moiety is an antibody capable of binding to the antigen.

35. The electrode as claimed in claim 34, which further comprises at least part of an antigen that is bound to the redox active species, wherein the antibody binding moiety is bound to the at least part of an antigen.

* * * * *